(12) United States Patent
Muraoka et al.

(10) Patent No.: US 6,573,406 B2
(45) Date of Patent: Jun. 3, 2003

(54) HIGH-PURITY ALKANOLAMINES AND THEIR PRODUCTION PROCESS

(75) Inventors: Kenji Muraoka, Kanagawa-ken (JP); Toshiaki Saito, Kanagawa-ken (JP); Yukio Kadono, Kanagawa-ken (JP)

(73) Assignee: Nippon Shokubai Co. Ltd., Osaka (JP)

( * ) Notice: Subject to any disclaimer, the term of this patent is extended or adjusted under 35 U.S.C. 154(b) by 0 days.

(21) Appl. No.: 10/053,911

(22) Filed: Jan. 24, 2002

(65) Prior Publication Data

US 2002/0120167 A1 Aug. 29, 2002

(30) Foreign Application Priority Data

Jan. 30, 2001 (JP) .......................................... 2001-020869

(51) Int. Cl.$^7$ ............................................ C07C 209/84
(52) U.S. Cl. ........................ 564/497; 564/498; 564/499
(58) Field of Search ................................ 564/497, 498, 564/499

(56) References Cited

U.S. PATENT DOCUMENTS

| | | | | |
|---|---|---|---|---|
| 5,424,482 A | * | 6/1995 | Overgaard et al. .............. | 564/2 |
| 5,866,719 A | * | 2/1999 | Desantis et al. ............. | 564/497 |
| 5,872,295 A | * | 2/1999 | Michelotti et al. .......... | 564/301 |

FOREIGN PATENT DOCUMENTS

JP 5-271699 10/1993 ........... C11D/10/02

OTHER PUBLICATIONS

Database CAPLUS on STN, Acc. No. 1989:526194, Golub et al., "Development of technology of high–purity monoethanolamine and analytical monitoring methods." Vysokochist. Veshchestva (1989), (1), p. 109–13 (abstract).*

Database CAPLUS on STN, Acc. No. 1976:132136, Karamian, 'An apparatus for continuous production of high–purity, bacteria–free, endoxin–free water for biomedical use.' Am. Lab. (1976), 8(3), p. 24–6, 28 (abstract).*

Database CAPLUS on STN, Acc. No. 1971:34072, Bom, 'Selection of alloys for multi–stage flash–distillation plant.' Brit. Corros. J. (1970), 5(6), p.258–63 (abstract).*

* cited by examiner

*Primary Examiner*—Brian Davis
(74) *Attorney, Agent, or Firm*—Sherman & Shalloway

(57) ABSTRACT

High-purity alkanolamines, whose iron content is less than 50 ppb, are provided. Said high-purity alkanolamines can be produced by covering with an alkanolamine-resistant material at least a part of the inner wall of equipment that contacts alkanolamines from the top of the distillation tower to the storage tank in producing a high-purity alkanolamine from a crude alkanolamine by using distillation towers.

1 Claim, 1 Drawing Sheet

HIGH-PURITY ALKANOLAMINES AND THEIR PRODUCTION PROCESS

FIELD OF APPLICATION IN INDUSTRIES

The present invention relates to high-purity alkanolamines and their production process. More specifically the present invention relates to a process to produce high-purity alkanolamines, whose metal content is very small, particularly iron content is less than 50 ppb.

PRIOR ART

Alkanolamines are used for a wide variety of application, for example, as intermediates for surface-active gents, agricultural chemicals, pharmaceuticals etc. or as cleaning agent for surfaces of metal, glass etc. Particularly monoethanolamine shows high peeling and cleaning properties to photoresist for semiconductor, liquid crystalline substance, solder flux, fat and oil etc. and is preferable as photoresist peeling agent, cleaning agent for liquid crystal cells, cleaning agent for solder flux, cleaning agent for degreasing of metallic products, cleaning agent for electronic parts, etc. For using for such applications, however, monoethanolamine of high purity, particularly with small metal content, is required (cf. Japanese Laid-Open Patent Publication No. 271699/1993).

By using conventional alkanolamine production facilities, however, it was difficult to produce monoethanolamine with small metal content due to its own strong metal-corrosive property (cf. Reference Example 1 given later).

Problems the Invention is going to Solve

One of the purposes of the present invention is to provide high-purity alkanolamines, whose iron content is less than 50 ppb Another purpose of the present invention is to provide a process to produce high-purity alkanolamines, particularly alkanolamines with very small metal content, by using conventional alkanolamine production facilities with only a simple improvement.

Means of Solving the Problems

Crude alkanolamine, for example, a reaction product, obtained by the reaction of ethylene oxide and ammonia and consisting of a mixture of monoethanolamine, diethanolamine and triethanolamine, is separated into each component by distillation for each application. According to the research of the present inventors it was found out that the metal content, particularly iron content, increases during distillation, particularly in the overhead product line at the top of the distillation tower, and its cause is the dissolution of metal components of materials such as stainless steel or iron, of which the piping is made. The present inventors, therefore, have succeeded in obtaining alkanolamines with very small metal content by covering with an alkanolamine-resistant material the inner wall of equipment that contacts alkanolamines (for example, piping etc.) after the top of the distillation tower. Thus, according to the present invention, there are provided high-purity alkanolamines, whose iron content is less than 50 ppb, and a production process of a high-purity alkanolamine characterized by covering with an alkanolamine-resistant material at least a part of the inner wall of equipment that contacts alkanolamines from the top of the distillation tower to the storage tank, in producing a high-purity alkanolamine by distillation of a crude alkanolamine.

MODE OF CARRYING OUT THE INVENTION

According to the present invention, the dissolution of metal components in the equipment material into alkanolamines is prevented by covering at least a part of the inner wall of equipment with an alkanolamine-resistant material, for example, resin, glass etc., preferably resin. As the above-mentioned resin, an alkali-resistant resin is preferable and there can be used, for example, polyethylene resin, polypropylene resin, polystyrene resin, fluororesin etc. The covering thickness can be suitably chosen to such an extent as to prevent the dissolution of metal components.

As representative examples of the alkanolamines of the present invention there can be mentioned monoethanolamine, diethanolamine, triethanolamine etc. Above all, monoethanolamine is preferably used. The present invention, therefore, will be described in mentioning monoethanolamine as example.

Monoethanolamine is obtained by separation through distillation from a reaction mixture containing monoethanolamine, diethanolamine, triethanolamine etc. obtained by the reaction of ethylene oxide and ammonia. In the present invention, at least a part of the inner wall of equipment that contacts monoethanolamine from the top of the distillation tower to the storage tank is covered with an alkanolamine-resistant material such as resin. The distillation tower mentioned here includes a distillation tower to separate monoethanolamine from a reaction mixture and a distillation tower to purify the separated monoethanolamine. And the equipment that contacts monoethanolamine from the top of the distillation tower to the storage tank includes the piping to transfer the distillate from the top of the distillation tower to the condenser, the piping to reflux a part of the condensate to the distillation tower, the piping to transfer the condensate to the next distillation tower, the piping to transfer the condensate as the product ethanolamine to the storage tank, and the storage tank. In the present invention, it is possible to cover all the inner wall of the above-mentioned piping and the storage tank and it is possible, too, to cover only the inner wall of the piping, excluding the storage tank.

BRIEF DESCRIPTION OF THE DRAWING

In the attached drawing,

FIG. 1 shows the route to finally transfer the distillate from the distillation tower for ethanolamine purification as the product ethanolamine to the storage tank. The distillate from the top of the distillation tower D is introduced to the condenser C through the line 1. Most of the condensate obtained here is transferred through the line 4, the pump P and the line 2 to the storage tank S and the remaining part is refluxed through the line 3 to the distillation tower D. Covering can be made on all the inner wall of the lines 1 to 4 and the storage tank S or only on the inner wall of the lines 1 and 2.

Figure 1:
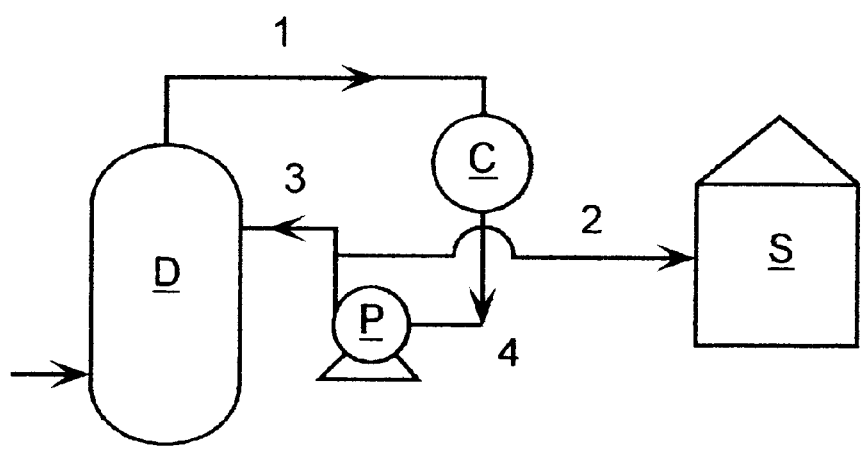
FIG. 1 is a flow diagram illustrating a mode of the present invention.

As the temperature inside the pipe of the line varies depending upon the distillation operation pressure of the distillation tower and is usually 40–200° C., it is preferable to cover with a fluororesin from the viewpoint of chemical resistance and heat resistance. The places that are necessary to be covered with a fluororesin, including the storage tank that contacts an alkanolamine for a long time, are places where temperature becomes usually higher than 20° C., particularly higher than 40° C., and above all higher than 60° C.

According to the process of the present invention it is possible to produce alkanolamines with very small metal content. Specifically it is possible to produce an alkanolamine, whose iron content and alkali metal content each is less than 50 ppb, and further an alkanolamine, whose iron content is less than 20 ppb. High-purity alkanolamines, whose iron content is less than 50 ppb, are preferable for cleaning agent for electronic parts.

Moreover, the process of the present invention is not restricted to the case of producing a purified ethanolamine from the crude ethanolamine obtained by the reaction of ethylene oxide and ammonia, but can be applied to reuse the used alkanolamine by purification in case of using an alkanolamine as cleaning agent for electronic parts.

Effect of the Invention

By the present invention it becomes possible to produce high-purity alkanolamines with very small metal content by a simple improvement of conventional alkanolamine production facilities.

EXAMPLE

Then the present invention will be described more specifically by mentioning examples. Iron content in ethanolamine was measured by using ICP-AES (inductively coupled plasma atomic emission spectroscopy) SPS1700VR made by Seiko Instruments Inc.

Example 1

Crude monoethanolamine (monoethanolamine purity: 40.9% by weight, iron content: 8.5 ppb), after separation of light fractions such as non-reacted substances, was introduced into the distillation tower D shown in FIG. 1 and distilled under the operation pressure of 10 torr. After the distillate had been condensed, a part of the condensate was refluxed to the distillation tower D and the remainder was transferred to the tank S. The inner wall of the pipes of the lines 1 and 2 (made of SUS316) had been covered with a fluororesin (PPFE, made by Nippon Valqua Industries, Ltd.). The temperature of the condensate transferred to the storage tank S was 60° C.

Iron content in monoethanolamine in the storage tank was measured as 10 ppb. No substantial increase in iron content was observed.

Referential Example 1

The same operation as Example 1 was conducted, except no covering with fluororesin was made on the inner wall of the pipes of the lines 1 and 2 in Example 1. Iron content in monoethanolamine in the storage tank was measured a 60 ppb. A remarkable increase in iron content was observed.

What is claimed is:

1. A production process of a high-purity alkanolamine characterized by covering with an alkanolamine-resistant fluororesin at least a part of the inner wall of equipment that contacts alkanolamines from the top of the distillation tower to the storage tank in producing a high-purity alkanolamine by distillation of a crude alkanolamine under the operation pressure of 10 torr.

* * * * *